(12) United States Patent
Lee et al.

(10) Patent No.: US 10,624,866 B2
(45) Date of Patent: Apr. 21, 2020

(54) COMPOSITION FOR PREVENTION OR TREATMENT OF CHRONIC PAIN COMPRISING EVANS BLUE

(71) Applicant: THE INDUSTRY & ACADEMIC COOPERATION IN CHUNGNAM NATIONAL UNIVERSITY (IAC), Daejeon (KR)

(72) Inventors: Won Hyung Lee, Daejeon (KR); Dong Woon Kim, Daejeon (KR); Jin Pya Hong, Daejeon (KR); Yu Hua Yin, Daejeon (KR)

(73) Assignee: THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 0 days.

(21) Appl. No.: 15/911,391

(22) Filed: Mar. 5, 2018

(65) Prior Publication Data
US 2019/0269633 A1 Sep. 5, 2019

(51) Int. Cl.
*A61K 31/185* (2006.01)
*A61P 29/00* (2006.01)

(52) U.S. Cl.
CPC ............ *A61K 31/185* (2013.01); *A61P 29/00* (2018.01)

(58) Field of Classification Search
None
See application file for complete search history.

(56) References Cited

U.S. PATENT DOCUMENTS

| 2002/0004493 A1* | 1/2002 | Crutcher | ............... A61K 31/70 514/56 |
| 2007/0099863 A1* | 5/2007 | Matute Almau | ....... A61K 31/00 514/47 |

FOREIGN PATENT DOCUMENTS

WO 2013/167743 11/2013

OTHER PUBLICATIONS

Driessen, B. et al., "Antinociceptive effect of intrathecally administered P2-purinoceptor antagonists in rats", Brain Research, 1994, vol. 666(2), pp. 182-188.
Ok, H.Y. et al., "Intrathecal Administration of Methylene Blue Reduces Pain Behavior in Neuropathic Rats", 42nd Annual Regional Anesthesiology & Acute Pain Medicine Meeting, 2017.

* cited by examiner

*Primary Examiner* — Bong-Sook Baek
(74) *Attorney, Agent, or Firm* — Ping Wang; Morris, Manning & Martin, LLP (57) ABSTRACT

The present disclosure relates to a pharmaceutical composition or food composition including Evans blue for prevention or treatment of chronic pain diseases. The administration of Evans blue according to the present disclosure can effectively reduce chronic pain, such as neuropathic pain. In particular, Evans blue targets mainly VNUT protein of dorsal root ganglia, which plays an important role in the secretion of ATP from the distal end of the afferent nerve and can relieve the pain using drugs continuously without side effects so that it can be efficiently used as an analgesic for various kinds of pain caused by chronic pain diseases.

2 Claims, 5 Drawing Sheets

COMPOSITION FOR PREVENTION OR TREATMENT OF CHRONIC PAIN COMPRISING EVANS BLUE

FIELD

The present disclosure relates to a pharmaceutical composition or food composition including Evans blue for prevention or treatment of chronic pain diseases.

BACKGROUND

Millions of people after injury or surgery and those suffering from diseases such as arthritis, cancer, and diabetes are afflicted with pain. Nociception (detection of noxious stimuli or harmful stimuli) provides significant biological objects. In other words, it makes living organisms to prepare for environmental hazards and induce pain sensation, reflex withdrawal, and complicated hyperactive and emotional responses, thereby protecting organisms from further damage. The noxious stimuli are detected by specialized high-threshold primary sensory neurons (nociceptors), in which the nociceptors transmit signals to the spinal cord and then transmit the same to the brain with the purpose of higher-level processing that leads to conscious awareness of sensation, called pain. The functional significance of pain perception is exemplified by individual defects in pain receptor, and no the patients who are inherently insensitive to pain can live past the twenties.

Pain may be divided in view of the occurrence area, cause, nature, and mechanism. For example, nociceptive pain is one classified by pathophysiological mechanism, is caused by tissue damage and tends to increase in proportion to harmful stimuli. Generally, the nociceptive pain is self-controlling type and has defensive biological functions by warning of ongoing tissue damage induced by harmful chemical, thermal, and mechanical stimuli. The nociceptive pain includes, for example, post-operative pain, pain associated with trauma, and pain associated with arthritis. On the other hand, neuropathic pain is one of inappropriate adverse reaction regardless of the degree of noxious stimulation, which is characterized by spontaneous pain, hyper-pain, and allodynia.

Pain may be divided into acute and chronic pain depending on the duration of pain. As a representative chronic pain disease, there are neuropathic pain, complex regional pain syndrome, postherpetic neuralgia, postoperative pain syndrome, and the like. Chronic pain is not merely an extension of the acute pain, and the degree of pain may be in non-proportion to the degree of original injury and be occurred spontaneously without stimulation. It is defined as chronic pain when the duration and severity of the pain are detrimental to the function or life of the patient, or the pain lasts over a period of normal tissue healing, usually over three months. The chronic pain is not a symptom, but a disease. The chronic pain is ruthless and cannot be personally controlled and can last for years and decades after the initial injury. The chronic pain is mainly neuropathic in nature and may include the damage of peripheral or central nervous system.

Among the various kinds of pain, neurogenic pain, neuropathic pain, is one that occurs even when there is no cause of injury or pain seemingly. The neuropathic pain is a general term for pain caused by neuronal damage or nervous system disorders such as nerve compression or nerve trauma caused by cancer, autoimmune disease or infection of herpes zoster. The neuropathic pain is chronic pain with clinical characteristics such as allodynia which responds to pain even by stimulation that does not cause pain in normal state, hyperalgesia which is more sensitive to painful stimuli, and spontaneous burning sensation without stimulation. Unlike beneficial acute pain, such neuropathic pain leads to more pain than the pain of the disease due to deformation of the nervous system that transmits pain.

Traditionally, such neuropathic pain has been thought to be caused by hyperexcitability of sensory neurons caused by degeneration of neurons. The causes of hyperexcitability of such sensory neurons are hypothesized as several causes such as 1) changes in homeostasis of the environment around the cell (extra-neuronal homeostasis) due to injury to neurons, 2) expression of sensory neuronal cell membrane ion channel and alteration of ion channel regulatory protein activity due to damage to neurons, 3) new formation of pain transfer circuit caused by synaptic reorganization, and 4) the hyperexcitation of sensory neurons due to the death of inhibitory interneurons.

It has been reported that 3% of the total population live in neuropathic pain. The most common neuropathic pain is hyperalgesia, hypersensitivity, neuropathy, diabetic neuropathy, neuritis, neuralgia, causalgia, allodynia, postherpetic neuralgia, neuromuscular compression, or the like, and in addition, pain associated with cancer, spinal cord injury, post-stroke pain, HIV-related neuropathy, and phantom limb pain. In the United States, it has been reported that the cost of disability related to neuropathic pain is about $40 billion annually, and it is urgent to develop a therapeutic agent for treating such neuropathic pain.

Currently, substances that reduce neurotic excitability or sensory axon conduction is administered against neuropathic pain. Various drugs are used, including antiepileptics, topical lidocaine, analgesics, non-steroidal anti-inflammatory agents, opiad, and the like. However, there are only few studies on substances that can effectively treat neuropathic pain. Because of differences in efficacy and side effects of drugs, it is challenging to select drugs to treat neuropathic pain, and there is a need for the development of novel therapeutic agents against neuropathic pain.

Meanwhile, Evans blue (EB) is harmless to human body and a blue-colloidal azo dye, which binds to albumin and stays in the blood for a long time. It is easy to measure Evans blue because it is less affected by hemolysis, and thus Evans blue is used to measure circulating blood volume. The role of Evans blue in chronic pain diseases or neuropathic pain has not yet been elucidated, and there is no research thereon.

SUMMARY

The present inventors, while having studied a novel therapeutic agent for chronic pain diseases, confirmed that Evans blue exhibited analgesic effects in chronic pain diseases and completed the present disclosure.

In addition, it has been revealed that Evans blue targets all neurons and microglia cells present in dorsal horn in the spinal cord and the vesicular nucleotide transporter (VNUT) of dorsal root ganglia cells, resulting in suppression of hyperexcitation of neuron in the dorsal horn in the spinal cord and relieving pain.

Therefore, the present disclosure has been made in an effort to provide a pharmaceutical composition including Evans blue as an active ingredient for prevention or treatment of chronic pain diseases.

Further, the present disclosure has been made in an effort to provide a food composition including Evans blue as an active ingredient for prevention or amelioration of chronic pain diseases.

Further, the present disclosure has been made in an effort to provide a method for preventing or treating chronic pain diseases, in which the method includes administering Evans blue to an object.

An exemplary embodiment of the present disclosure provides a pharmaceutical composition including Evans blue as an active ingredient for prevention or treatment of chronic pain diseases.

Another exemplary embodiment of the present disclosure provides a food composition including Evans blue as an active ingredient for prevention or amelioration of chronic pain diseases.

Yet another exemplary embodiment of the present disclosure provides a method for preventing or treating chronic pain diseases, in which the method includes administering Evans blue to an object.

According to the exemplary embodiments of the present disclosure, the administration of Evans blue can efficiently reduce chronic pain. In particular, Evans blue targets mainly VNUT protein of dorsal root ganglia, which plays an essential role in the secretion of ATP from the distal end of the afferent nerve and can relieve the pain using drugs continuously without side effects so that it can be efficiently used as an analgesic for various kinds of pain caused by chronic pain diseases.

The foregoing summary is illustrative only and is not intended to be in any way limiting. In addition to the illustrative aspects, embodiments, and features described above, further aspects, embodiments, and features will become apparent by reference to the drawings and the following detailed description.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

DETAILED DESCRIPTION OF THE INVENTION

Hereinafter, the present disclosure is described in detail.

The present disclosure provides a pharmaceutical composition including Evans blue as an active ingredient for prevention or treatment of chronic pain diseases.

Since Evans blue of the present disclosure may efficiently reduce chronic pain and thus may be useful as an analgesic for various pain caused by chronic pain diseases. Herein, the Evans blue can be administered as a composition including Evans blue as an active ingredient.

In the present disclosure, the "chronic pain disease" refers to a more intense pain that affects one or more parts of the body and lasts for more than three months and includes pain syndromes that may vary in its intensity over time. The chronic pain diseases include, but are not limited to, neuropathic pain, complex regional pain syndrome, postherpetic neuralgia, post-spinal surgery pain syndrome, osteoarthritis and the like.

In the present disclosure, the "neuropathic pain" is preferably induced by peripheral nerve injury or central nerve injury. The neuropathic pain includes, but is not limited to, peripheral nervous system disorder or injury, multiple sclerosis including spinal cord nerve injury, spinal cord injury, hyperalgesia, hypersensitivity, neuropathy, diabetic neuropathy, neuritis, neuralgia, causalgia, allodynia, postherpetic neuralgia, neuromuscular compression, pain associated with cancer, alcoholism, atypical facial pain, post herpetic neuralgia, post-stroke pain, HIV-related neuropathy, osteoarthritis, and phantom limb pain. The neuropathic pain is a model of illustrating mechanism of chronic pain.

In the present disclosure, Evans blue is characterized by increasing threshold of pain.

In the present disclosure, Evans blue was injected into the spinal canal of an animal model of neuropathic pain, and Von Frey filament test was performed to confirm that the pain threshold was increased, in other words, the pain was reduced, upon treatment with Evans blue.

In addition, Evans blue targets all neurons and microglia cells present in the dorsal horn of the spinal cord and the vesicular nucleotide transporter (VNUT) of the dorsal root ganglia cells, resulting in inhibition of hyperexcitation of neurons in the dorsal horn in the spinal cord.

Therefore, in the present disclosure, Evans blue is characterized by inhibiting the hyper-excitation of excitatory neurons distributed in the dorsal horn in the spinal cord, and the inhibition of hyperexcitation of excitatory neurons is induced by functional inhibition of at least one site selected from the group consisting of vesicular nucleotide transporter (VNUT) of dorsal root ganglia and excitatory neurons and microglia cells present in the dorsal horn of the spinal cord.

The composition of the present disclosure includes a pharmaceutically acceptable carrier. The pharmaceutically acceptable carrier included in the pharmaceutical composition of the present disclosure may be conventionally used in formulation, which includes, but is limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, saline, phosphate buffered saline (PBS), medium or the like.

The term "pharmaceutically acceptable" refers to a composition that is physiologically acceptable and does not typically cause an allergic reaction or the like when administered to a human.

The pharmaceutical composition of the present disclosure may further include a lubricant, a wetting agent, a sweetening agent, a flavoring agent, an emulsifying agent, a suspending agent, a preservative, etc. in addition to the components as described above. Those described in the known prior art documents may be referred as the suitable pharmaceutically acceptable carrier and preparation.

In the case of preparation for parenteral administration, it may be formulated by a method known in the art in the form of an injection. These formulations may be referred to those described in prior art documents generally known in pharmaceutical chemistry.

The pharmaceutical composition of the present disclosure may be administered orally or parenterally, for example, by intrathecal, intravenous, intramuscular, intraarterial, intramedullary, intradermal, intracardiac, transdermal, subcutaneous, intraperitoneal, intranasal, intestinal, topical, sublingual or rectal administration, preferably oral or subcutaneous administration, and may be used together, simultaneously, sequentially, including additional elements for the treatment of chronic pain or neuropathic pain.

The "intrathecal administration" refers to administering the pharmaceutical composition of the present disclosure into the spinal cord to allow the active ingredient contained in the pharmaceutical composition for the prevention or treatment of chronic pain disease, such as neuropathic pain, to be delivered into the spinal cord.

The composition of the present disclosure is administered in a pharmaceutically effective amount. In the present disclosure, the term "pharmaceutically effective amount" refers to an amount sufficient to treat a disease, and the effective dose level may be determined according to factors including the severity of the disease; age, weight, health, and gender of the patient; the sensitivity of the patient to the drug; administration time, route of administration and rate of release; treatment period; drugs used in combination with or co-used with the composition of the present disclosure used and factors known to other medical field. Preferably, the pharmaceutical composition of the present disclosure may have an effective amount varying depending on the severity of the disease, but preferably an effective amount of 150 to 5000 μg/60 kg/day, more preferably 500 to 1500 μg/60 kg/day may repeatedly be administered several times a day. The dosage of the composition does not limit the scope of the present disclosure in any scheme.

The pharmaceutical composition for the prevention or treatment of the chronic pain disease such as the neuropathic pain of the present disclosure may be administered to mammals, including, but not limited to, humans and mammals except for humans for example.

Further, the present disclosure provides a food composition including Evans blue as an active ingredient for prevention or amelioration of chronic pain diseases.

Evans blue according to the present disclosure may be added to foods, beverages, or the like for the purpose of preventing or ameliorating chronic pain disease such as neuropathic pain. The foods include, for example, various kinds of foods, beverages, gums, teas, vitamin complexes, functional food, etc. and includes special nutrient foods (e.g., milk formulas, infants formulas, etc.), processed meat products, health supplement foods, seasoned foods (e.g., soy sauce, bean paste, red pepper paste, mixed soy paste, etc.), sauces, confectioneries (e.g., snacks), candies, chocolate, gums, ice-creams, dairy products (e.g., fermented milks, cheeses, etc.), other processed foods, beverages (e.g., fruit juices, vegetable juices, fermented beverages, etc.), and natural seasonings but are not limited thereto. The foods, beverages, or food additives may be prepared according to a conventional preparing method.

The term "functional food" refers to a processed food which is designed to express sufficiently the body's control function for the living body regarding the biological defense rhythm, prevention of diseases, recovery thereof, etc. which a food group or food composition has, which has been imparted with added value to function or express the function of the food for particular purpose using physical, biochemical, biotechnological techniques, etc. Specifically, it may be a health functional food. The functional food may further include a sitologically acceptable food supplement additive, and may further include a proper carrier, excipient, and diluent, which are commonly used in the preparation of functional foods.

The amount of Evans blue in the food or beverage may be from 0.001% by weight to 90% by weight with respect to the total food weight, and preferably from 0.1% by weight to 50% by weight with respect to the total food weight. In the case of beverages, it may be included in a proportion of 0.001 g to 2 g with respect to 100 ml, preferably 0.01 g to 0.1 g with respect to 100 ml, but in the case of long-term intake for health and hygiene purposes or health control purpose, the amount may be the range or less. Since the active ingredient has no problem in terms of safety, it can be used in an amount of the range or more. Thus, it is not limited to the range.

The food composition of the present disclosure may further include various flavors or natural carbohydrates, etc., as conventional food compositions. Examples of natural carbohydrates may include conventional sugars such as: monosaccharides, e.g., glucose, fructose, etc.; disaccharides, e.g., maltose, sucrose; and polysaccharides, e.g., dextrin, cyclodextrin, etc.; and sugar alcohol such as xylitol, sorbitol, erythritol, etc. As a sweetener, natural sweeteners such as thaumatin, *stevia* extracts (e.g., rebaudiocide A, glycyrrhizin, etc.), and other synthetic sweeteners (saccharin, aspartame, etc.) may be used advantageously.

The food composition may contain various nutrients, vitamins, minerals (electrolyte), flavoring agents such as synthetic flavoring agents and natural flavoring agents, coloring agents and improving agents (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages, etc.

Further, the present disclosure provides a method for preventing or treating a chronic pain disease, comprising administering Evans blue to an object.

Evans blue may be administered through the various route such as topical (including buccal, sublingual, percutaneous, and intraocular administration), parenteral (including subcutaneous, intradermal, intravascular and intraarticular administration), or percutaneous administration.

The object may include, but is not limited to, canine-family, feline-family, wild boar-family, bovine-family, deer-family, giraffe-family, peccary-family, camel-family, hippopotamus-family, horse-family, tapir-family, rhinoceros-family, weasel-family, rabbit-family, rodents, and primates.

The contents of the present disclosure as described above are equally applied with each other unless they are mutually contradictory, and it is also within the scope of the present disclosure that those skilled in the art make appropriate modifications. Hereinafter, the present disclosure will be described in detail through experimental examples and exemplary embodiments, but the scope of the present disclosure is not limited to the following experimental examples and embodiments.

Example 1. Confirmation of Analgesic Effect of Evans Blue in an Animal Model of Neuropathic Pain 1-1. Preparation of Animal Models 5-week-old male SD white rats (Sprague-Dawley rats, 150 to 180 g) were purchased and were kept in an environment where each of night and day was continuously kept for 12 hours, and the temperature was maintained at 22±2° C. Further, water and feed were freely available for rats, and the rats were fed three or less per cage. At 6 weeks of age after adapted in an experimental environment for 7 days before the experiment, the rats responsive to stimulation of 8 g or more of von Frey filament were only selected, and then the spinal nerve ligation (SNL) procedure was performed thereon, inducing neuropathic pain (NPP).

Figure 1A:
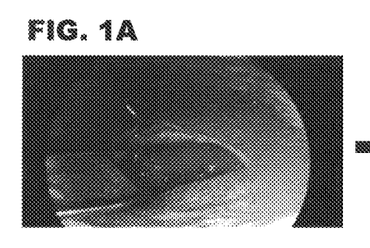
FIGS. 1A-1D show views illustrating a spinal nerve ligation (SNL) surgical procedure of a rat and a schematic view thereof.
Figure 1B:
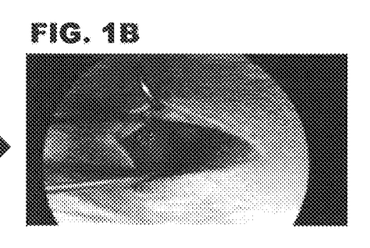
Figure 1C:
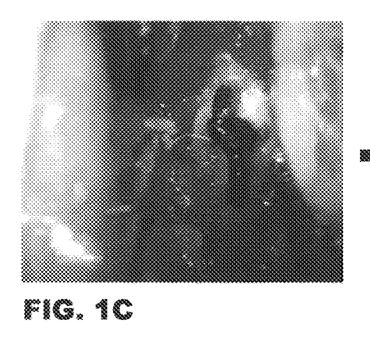
Figure 1D:
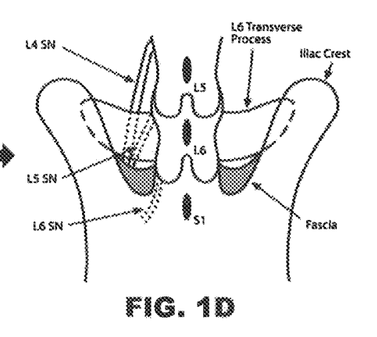

More specifically, after general anesthesia with respiratory anesthesia with isoflurane, the left lumbar (L6) intervertebral disc was carefully removed for differentiation of the L4 and L5 spinal nerves (FIGS. 1A to 1B), and then the L5 spinal nerve was ligated with a silk suture thread (3-0), and the wound was sutured to prepare an experimental animal model of SNL neuropathic pain (FIGS. 1C to 1D).

FIGS. 1A-1D shows views illustrating a spinal nerve ligation (SNL) surgical procedure of such rat and a schematic view thereof.

1-2. Confirmation of the Analgesic Effect of Evans Blue Through Behavioral Experiments In Vivo The analgesic effect of Evans blue of the present disclosure was confirmed by measuring mechanical hyperalgesia using the animal model of neuropathic pain. The von Frey filament test (test for mechanical allodynia) is a method for measuring the degree of mechanical allodynia after animal pain modeling. The rats were placed in an acrylic box disposed on a wire mesh test bench with a mesh size of 2×2 mm and adapted for at least 15 minutes. After the rats became quiet in movement, the pain threshold values (g) of the rat were evaluated using the von Frey filaments (Stoelting, USA) having a thickness of 0.4, 0.6, 1, 2, 4, 6, 8, and 15 g. It was considered positive when the filament was contacted vertically to the left affected paw for 5 to 6 seconds, and then the rat showed a fast avoidance reaction or the rat jerked suddenly or licked its paw while lifting the hair. The central part thereof was stimulated with von Frey filaments. When there was a positive reaction, stimulation was performed with weak filaments. When there was no positive reaction, stimulation was performed with strong filaments. As a result, the reduction of the pain threshold for the von Frey filament test on the seventh day after the pain model surgery was the maximum.

Figure 2:
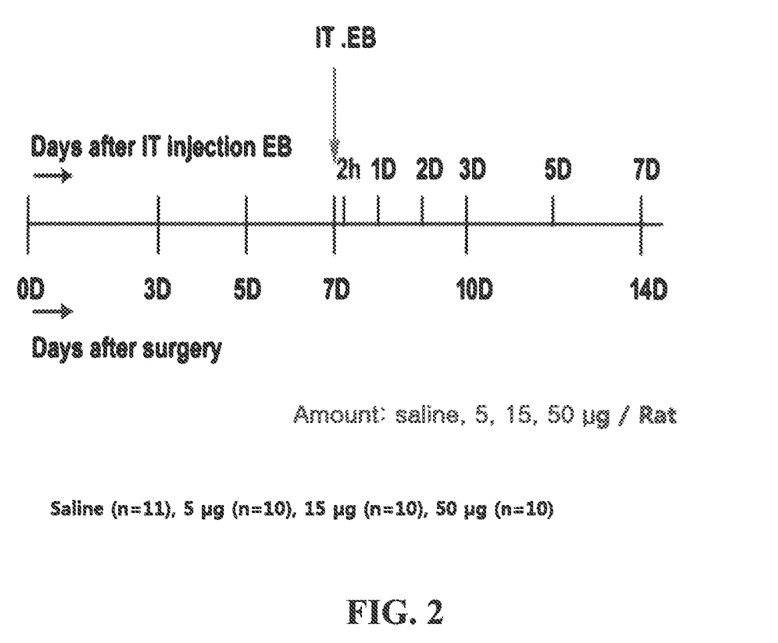
FIG. 2 is a view illustrating experimental process for confirming analgesic effect according to administration of Evans blue.

From the seventh day when the reduction of the pain threshold for the von Frey filament test after the pain model surgery was the maximum, Evans blue (EB) was injected intrathecal injection with a Hamilton syringe, and the hind paw of the mouse was stimulated with the von Frey filament to the measure minimum pain threshold. Changes in pain threshold were measured after 2 hours, 1 day, 2 days, 3 days, 5 days, and 7 days. At this time, 10 μl physiological saline was administered to the control group, and Evans blue was administered at various concentrations (5, 15, and 50 μg/10 μl). Such an experimental process is shown in FIG. 2, and the results are shown in FIG. 3.

Figure 3:
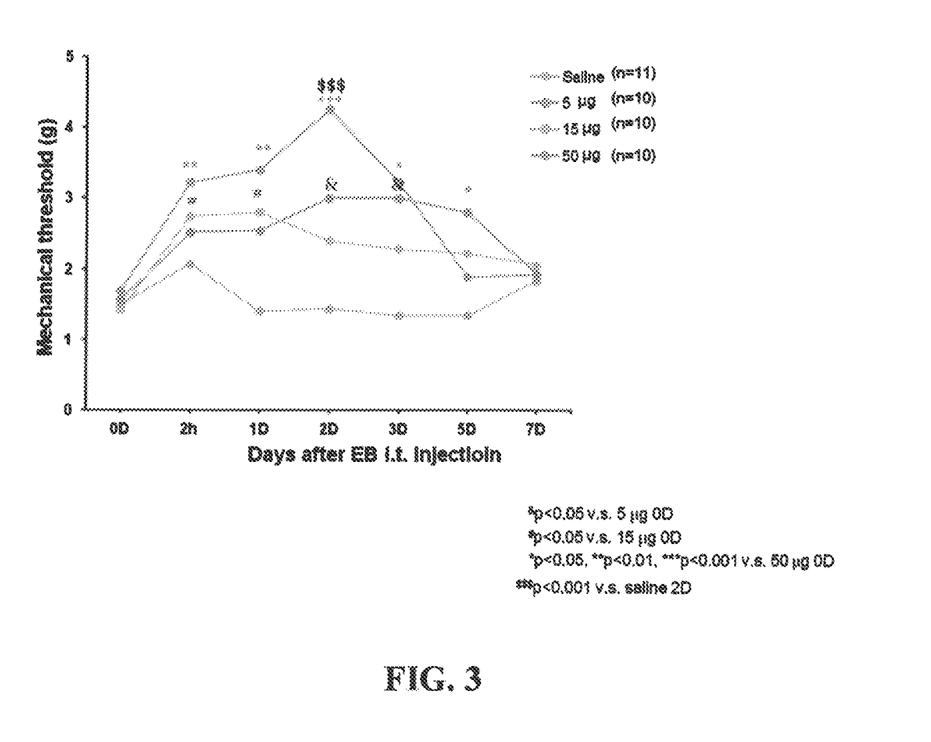
FIG. 3 is a graph illustrating analgesic effect according to the administration of Evans blue in spinal nerve ligation model.

As shown in FIG. 3, it was confirmed that there was almost no analgesic effect at all times in the control group treated only with physiological saline, whereas the analgesic effect on pain was overall increased meaningfully in the experimental group treated with Evans blue. Specifically, it was confirmed that the 5 μg-administrated group showed a significant increase in the intensity of pain on the 2nd and 3rd day ($p<0.05$) than before Evans blue treatment (0D). It was confirmed that 15 μg-administrated group showed a significant increase in the intensity of pain after 2 hours and the 1st day ($p<0.05$) than before Evans blue treatment (0D). It was confirmed that 50 μg-administrated group showed a significant increase in the intensity of pain after 2 hours and the 1st day ($p<0.01$), the 2nd day ($p<0.001$), the 3rd day, the 5th day ($p<0.05$), than before Evans blue treatment (0D) and showed a significant increase in the intensity of pain on the 2nd day ($p<0.001$) compared to the control group treated with physiological saline. The analgesic effect peaked on the 3rd day and gradually decreased thereafter. This study confirmed the pain relief effect of Evans blue.

Example 2. Confirmation of Action Mechanism of Evans Blue

Since it was confirmed that Evans blue relieves neuropathic pain in Example 1, the action mechanism of the analgesic effect of Evans blue was confirmed. According to prior art studies, there are three targets of Evans blue. The first is the vesicular nucleotide transporter (VNUT) present in the neural end and cell body of the afferent neuron of the dorsal root ganglia (DRG), the second is the excitatory neuron present in the dorsal horn of the spinal cord, and the last is the microglia cell distributed in the dorsal horn of the spinal cord. The following experiment was performed to confirm these three possibilities.

2-1. Verification of Targeting VNUT of the Dorsal Root Ganglia and Dorsal Horn of the Spinal Cord by Evans Blue To verify targeting VNUT of the dorsal root ganglia and dorsal horn of the spinal cord by Evans blue in vivo, VNUT was immune-stained, and Evans blue was administered in vivo to confirm whether it was targeted.

Specifically, it was immune-stained with VNUT antibody (green) to examine the expression of VNUT in the dorsal root ganglia and dorsal horn of the spinal cord. Evans blue was injected on the 7th day after the pain model surgery. On 2nd day after the injection of Evans blue, the white rat was anesthetized by intraperitoneal injection of sodium pentobarbital (100 mg/Kg). Then the phosphate buffer solution (PBS, pH 7.4) was intracardiac-perfused to entirely remove the blood, followed by perfusion with 4% paraformaldehyde to fix the result. Then, the spinal cord sites (L4 to L6) were carefully taken out, post-fixed in the same fixative overnight, and immersed in a 30% sucrose solution. Then, the tissues obtained by frozen sectioning of the spinal cord at 30 m were subjected to the normal serum blocking and then incubated overnight at 4° C. with VNUT (1:500; ABN 83; milipore) antibody. The next day, the result was washed with PBS and incubated with the cy2-conjugated secondary antibody (1:400) for 2 hours, and then the nuclear thereof was stained with DAPI. The tissues were attached to a slide glass and photographed using a confocal microscope (Leica, TCS SP8). The results are shown in FIGS. 4A-4G.

Figure 4A:
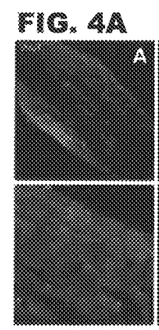
FIGS. 4A to 4F show the result of confirming that Evans blue targets the VNUT of the dorsal root ganglia (FIGS. 4A to 4C) and the dorsal horn of the spinal cord (FIGS. 4D to 4F)
Figure 4B:
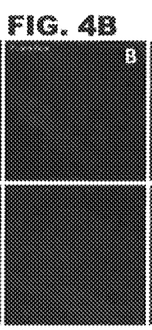
Figure 4C:
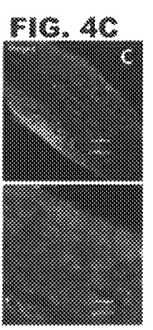
Figure 4D:
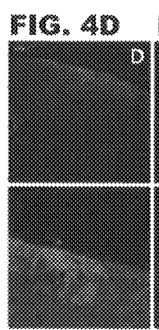
Figure 4E:
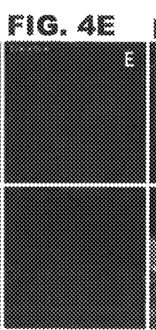
Figure 4F:
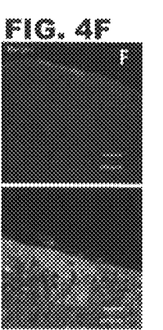
Figure 4G:
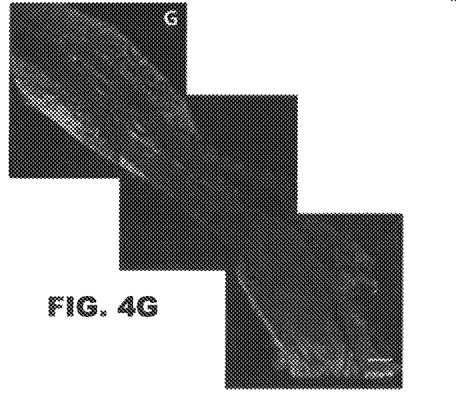
FIG. 4G shows the result of confirming the signal of calretinin expressed in the inhibitory neurons distributed in the dorsal horn lamina I and II in the spinal cord.

As shown in FIGS. 4A to 4C, it was confirmed that the signal of Evans Blue overlaps in the axon and the axon terminal, the cell body where the VNUT is expressed in the dorsal root ganglia. In addition, vGluT2 (a marker of excitatory vesicle) was stained around the cell body of neurons targeted by Evans Blue in the dorsal horn lamina I and II in the spinal cord (FIGS. 4D to 4F). On the other hand, calretinin expressed in inhibitory neurons distributed in laminas I and II did not overlap with Evans blue (FIG. 4G). It was confirmed that Evans blue targets VNUT in the dorsal root ganglia and dorsal horn of the spinal cord.

2-2. Verification of Targeting Excitatory Neuron Distributed in Dorsal Horn of the Spinal Cord by Evans Blue To determine whether Evans Blue targeted the neurons of the dorsal horn in the spinal cord, the spinal cord tissue injected with Evans blue was stained with NeuN, a marker for identifying neurons. Next, the immunostaining was performed with a vGluT2 marker to confirm that the neurons targeted by Evans Blue were excitatory neurons. In addition, since inhibitory neurons located in the spinal cord laminas I to III are also important neurons involved in pain signal transduction and pain activation, the immunostaining was performed with a marker of calretinin for confirming that Evans Blue also targets inhibitory neurons. Tissues were attached to a slide glass using the same tissue as in Example 2-1, and photographed using a confocal microscope (Leica, TCS SP8). Specifically, the results are shown in FIGS. 5A-5I.

Figure 5A:
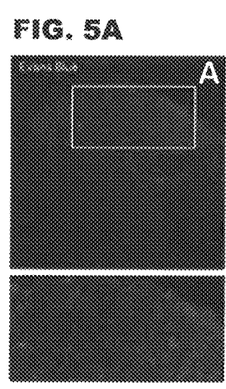
FIGS. 5A to 5F show the result of confirming that Evans blue targets the dorsal horn neurons in the spinal cord (FIGS. 5A to 5C) and the excitatory neurons distributed in the dorsal horn of the spinal cord (FIGS. 5D to 5F)
Figure 5B:
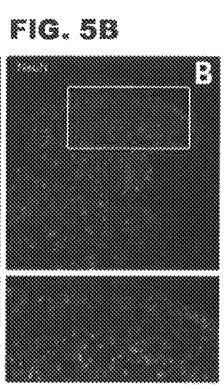
Figure 5C:
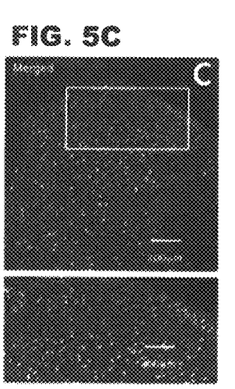
Figure 5D:
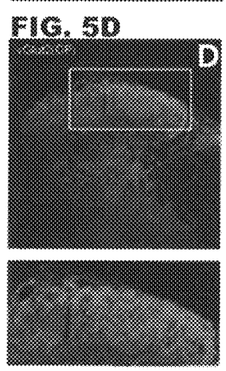
Figure 5E:
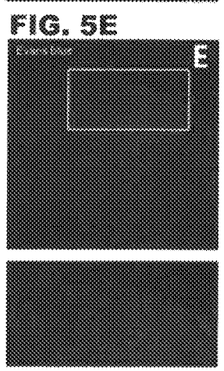
Figure 5F:
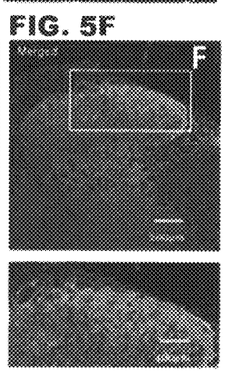
Figure 5G:
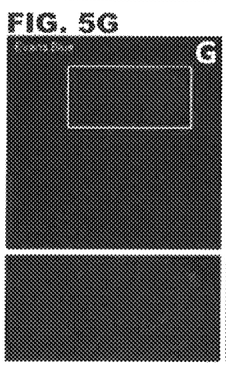
FIGS. 5G to 5I shows the result of confirming signal of calretinin expressed in the inhibitory neurons.
Figure 5H:
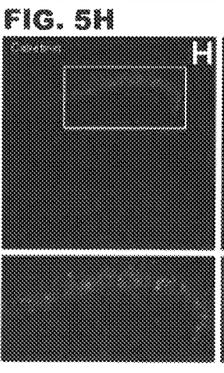
Figure 5I:
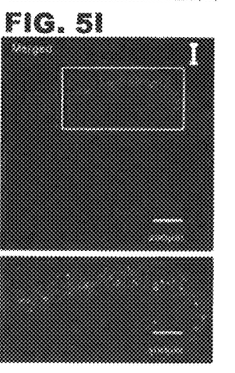

As shown in FIGS. 5A to 5C, it was confirmed that most signals of NeuN, which is a neuron marker, overlapped with those of Evans blue. It was confirmed that vGluT2, a marker of excitatory neurons, was stained around the cell bodies of neurons targeted by Evans Blue in the dorsal horn laminas I and II in the spinal cord. It was confirmed that Evans blue targeted excitatory neurons located in the dorsal horn of the spinal cord due to almost same as the neurons targeted by Evans blue (FIGS. 5D to 5F). Meanwhile, it was confirmed that Evans blue did not target inhibitory neurons since calretinin expressed in inhibitory neurons distributed in laminas I and II did not overlap with neurons targeted by Evans blue (FIGS. 5G to 5I).

2-3. Verification of Targeting Microglial Cell Present in Dorsal Horn of the Spinal Cord by Evans Blue Immunostaining was performed with Iba-1 antibody, a microglia cell marker, to confirm whether Evans Blue inhibits the activation of microglial cells by binding to the receptor of microglia cells (for example, P2X receptor) and thus interfering with the binding of ATP secreted at the ends of posterior neurons. In addition, immunostaining was performed with GFAP, an astrocytic cell marker, to confirm whether Evans Blue targets astrocyte, another astrocytic cell. In the experiment, tissues were attached to a slide glass using the same tissue as in Example 2-1, and photographed using a confocal microscope (Leica, TCS SP8). Specific results are shown in FIGS. 6A-6F.

Figure 6A:
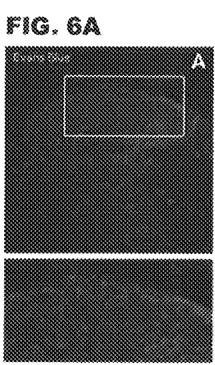
FIGS. 6A to 6C show the result of confirming that Evans Blue targets microglia cells present in the dorsal horn of the spinal cord.
Figure 6B:
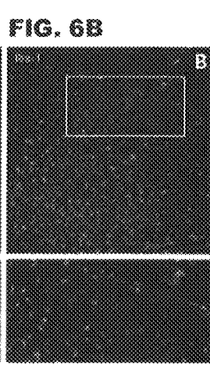
Figure 6C:
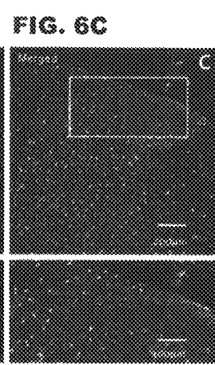
Figure 6D:
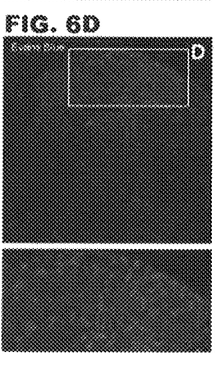
FIGS. 6D to 6F show the result of confirming that Evans Blue targets astrocytes.
Figure 6E:
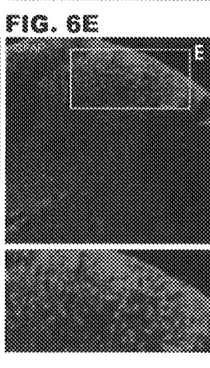
Figure 6F:
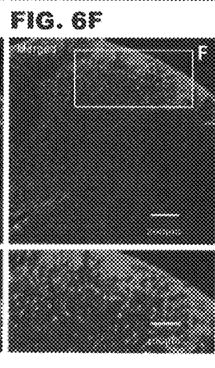

As shown in FIGS. 6A to 6C, it was confirmed that the signal (green) of Iba-1, which is a marker of microglial cells, partially overlapped with the signal of Evans blue in the laminas I to III. As a result, it was confirmed that Evans Blue bound to the receptor of microglia cells to lower the activity of microglial cells, thereby alleviating pain. However, it was confirmed that the signal (green) of GFAP, a marker of astrocytes, did not overlap with those of Evans Blue at all (FIGS. 6D to 6F). Those confirmed that Evans blue did not target astrocytes.

As a result, it was confirmed that Evans blue targets mainly VNUT protein of dorsal root ganglia, which plays a vital role in the secretion of ATP from the distal end of the afferent nerve and thus can relieve the pain using drugs continuously without side effects.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A method for treating a neuropathic pain, the method comprising intrathecally administering Evans blue to a subject in need thereof, wherein the neuropathic pain is at least one selected from the group consisting of hyperalgesia, neuropathy, diabetic neuropathy, neuritis, neuralgia, causalgia, allodynia, postherpetic neuralgia, neuromuscular compression, pain associated with cancer, atypical facial pain, herpetic neuralgia, post-stroke pain, osteoarthritis and phantom limb pain.

2. The method for treating a neuropathic pain of claim 1, wherein the neuropathic pain is induced by peripheral nerve injury or central nerve injury.

* * * * *